United States Patent [19]

Prible

[11] Patent Number: 4,752,312
[45] Date of Patent: Jun. 21, 1988

[54] HYDROCARBON GAS PROCESSING TO RECOVER PROPANE AND HEAVIER HYDROCARBONS

[75] Inventor: Donald E. Prible, Houston, Tex.
[73] Assignee: The Randall Corporation, Houston, Tex.
[21] Appl. No.: 9,168
[22] Filed: Jan. 30, 1987
[51] Int. Cl.$^4$ ................................................ F25J 3/02
[52] U.S. Cl. ............................................ 62/25; 62/39; 62/44
[58] Field of Search ...................... 62/9, 11, 23, 24, 25, 62/29, 30, 32, 36, 38, 39, 42, 44

[56] References Cited

U.S. PATENT DOCUMENTS

| | | | |
|---|---|---|---|
| 3,989,478 | 11/1976 | Jones | 62/36 X |
| 4,140,504 | 2/1979 | Campbell et al. | 62/38 X |
| 4,157,904 | 6/1979 | Campbell et al. | 62/38 X |
| 4,278,457 | 7/1981 | Campbell et al. | 62/38 X |
| 4,453,956 | 6/1984 | Fabbri et al. | 62/44 X |
| 4,519,824 | 5/1985 | Huebel | 62/30 X |

Primary Examiner—Steven E. Warner
Attorney, Agent, or Firm—William W. Habelt

[57] ABSTRACT

A cryogenic process for recovering propane and heavier hydrocarbons from natural gas streams or similar refinery or process streams containing lighter hydrocarbons such as methane and ethane. In the process disclosed, the gas to be separated is cooled which may include some condensation, in which case the condensate is separated from the vapor and fed to a lower region of all the fractionating column. The cooled vapor from the separator is split into two streams. One portion of the split vapor stream is work expanded to a midpoint of the fractionating column, while another portion of the split vapor stream is further cooled causing partial condensation, the condensate being separated and fed to the fractionation column above the feed from the first work expander, and the vapor being work expanded through a second expander and fed to the top of the fractionator as reflux.

3 Claims, 2 Drawing Sheets

HYDROCARBON GAS PROCESSING TO RECOVER PROPANE AND HEAVIER HYDROCARBONS

BACKGROUND OF THE INVENTION

The present invention relates generally to the processing of hydrocarbon gas streams to recover a desired condensable portion thereof, and, in particular, to an improved cryogenic gas separation process to recover propane and heavier hydrocarbons from a hydrocarbon gas stream such as natural gas or similar refinery or process gas streams.

The market demand and price for propane and heavier hydrocarbon liquids has remained such that it is most always economical to recover these compounds from natural gas or similar refinery or process streams. However, this has not been the case for ethane. The demand and price for ethane has fluctuated tremendously such that there are extended periods when it is ore economical to leave the ethane in fuel gas and only recover the propane and heavier hydrocarbons. Also, there are market locations where it may never be economical to recover ethane. Thus, there is a demand for processes which recover propane and heavier hydrocarbons from a hydrocarbon gas stream, while rejecting the ethane and lighter components to the residue or fuel gas.

Several variations of prior art cryogenic hydrocarbon separation processes are disclosed in U.S. Pat. Nos. 4,140,504; 4,157,904; and 4,278,457. In U.S. Pat. No. 4,157,904, for example, a process is disclosed for cryogenically separating a hydrocarbon gas stream to recover ethane and heavier hydrocarbons. As disclosed therein, the gas to be separated is precooled at a high pressure of about 900 psia to cause partial condensation. The condensate liquid and vapor are then separated. A first portion of the vapor is expanded to a lower pressure and fed to the demethanizer column. A second portion of the vapor is first cooled by passing in heat exchange relationship with the residue gas from the demethanizer column and then passed through an expansion valve to the demethanizer column at locations either above or below the point of injection of the first portion of expanded vapor depending upon the exact temperature conditions. The condensate from the separator is further cooled and then split into two streams. One stream is expanded to a lower pressure and passed to a lower region of the demethanizer, while the other stream is directly mixed with the second portion of vapor from the separator prior to further cooling and expansion. Ethane recovery is said to be on the order of 90% or better, with propane recovery said to be on the order of 98%.

As most of the prior art processes described in the aforementioned patents, and in particular the aforedescribed process, are designed primarily for high ethane recovery, as opposed to ethane rejection, these prior artprocesses are believed not suitable without modification to efficiently recover propane and heavy hydrocarbons from a mixed hydrocarbon gas stream while rejecting lighter hydrocarbon liquids, in particular ethane.

SUMMARY OF THE INVENTION

It is an object of the present invention to provide a cryogenic separation process for recovering propane and heavier hydrocarbons from a mixed hydrocarbon gas stream while rejecting lighter hydrocarbons, including ethane.

In the process of the present invention, the feed gas is cooled via residue gas resulting in partial condensation of the feed gas. The condensate liquid in the cooled feed gas is separated from the vapor and expanded through a valve to a lower pressure and passed to the lower section of the column. The vapor is split into two portions with a first portion being expanded through a work-expansion machine to a lower pressure and then fed to the column as a midpoint feed. The second portion of vapor is further cooled with residue gas causing partial condensation of the vapor. The vapor and liquid from the cooled second portion of vapor are separated and the liquid is expanded through a valve to a lower pressure and supplied to a midpoint section of the column. The remaining vapor is expanded through a second work-expansion machine to a lower pressure and passed to the top of the column as reflux. The partial condensing and separation of vapor and liquid, prior to the second expander, produces a vapor with a very small amount of propane which is an excellent advantage for the top column reflux feed. Power from the work expansion machines is used to compress either residue gas or inlet feed gas to higher pressures.

BRIEF DESCRIPTION OF THE DRAWING

A more thorough understanding of the present invention will be obtained from the following description of a preferred embodiment of the process of the present invention with reference to the accompanying drawing wherein.

DESCRIPTION OF THE PREFERRED EMBODIMENT

Figure 1:
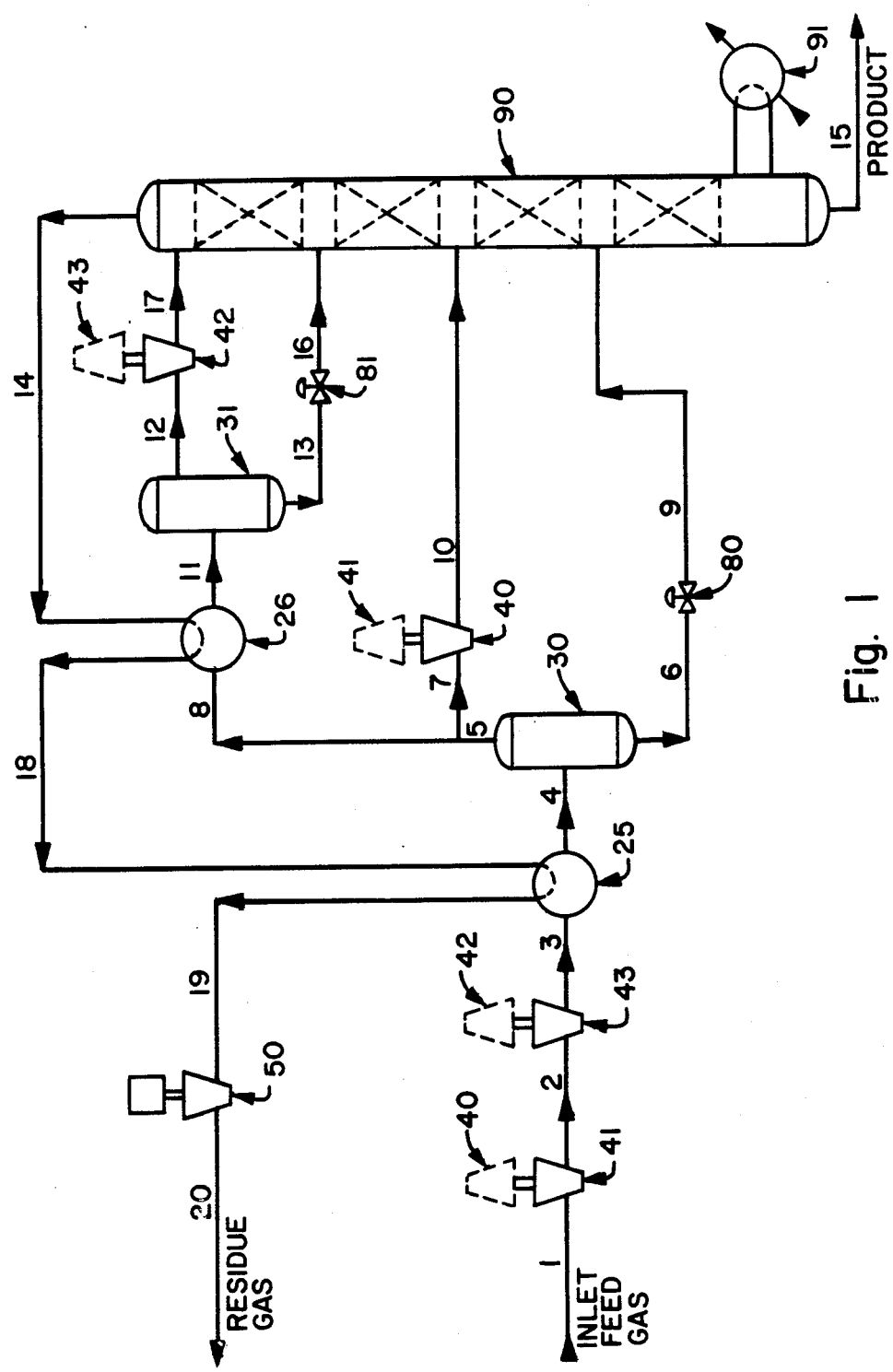
FIG. 1 is a schematic flow drawing illustrating the process of the present invention carried out using two work-expansion machines.

Referring now to FIG. 1, a mixed hydrocarbon gas enters the process as stream 1 at 485 psia and 60° F. The feed gas stream 1 has been pretreated as necessary to remove water and any other contaminants required such as carbon dioxide or sulphur compounds. Feed gas stream 1 is compressed via compressors 41 and 43 to provide a higher pressure feed gas stream 3 having a pressure of 643 psia and a temperature of 105° F. The compressors 41 and 43 are connected respectively to the shafts of the work-expansion machines 40 and 42. In this manner, power extracted in the work-expansion machines 40 and 42 is used to drive the compressors 41 and 43.

The feed gas stream 3 is then cooled via residue gas stream 18 in heat exchanger 25 to a temperature of 25° F. at 638 psia so as to cause a partial condensation of hydrocarbon components in stream 3. The condensate liquid produced as a result of this cooling are separated from the remaining vapor in separator vessel 30 and fed to the bottom of column 90 via valve 80. The vapor portion from vessel 30, identified as stream 5, is split into a first vapor stream 7 and a second vapor stream 8. Vapor stream 7 is passed through work-expansion machine 40 thereby forming a colder partially condensed stream 10 at −55° F. and 249 psia which is then fed to the lower middle portion of column 90. Vapor stream 8, however, is further cooled and partially condensed in heat exchanger 26 by passing in heat exchange relationship with cold residue gas 14 thereto forming stream 11 at −104° F. and 631 psia. Stream 11 is passed to separator vessel 31 and separated into vapor stream 12 and condensate liquid 13. Liquid 13 is flashed across valve 81 to 249 psia and −154° F. and fed to the upper middle portion of column 90. Vapor stream 12 is expanded through work-expansion machine 42 to 249 psia and −162° F. and fed to the top of column 90.

Fractionation column 90 in combination with reboiler 91 comprises a deethanizer. The hydrocarbon liquids collecting in the bottom region of the fractionation column 90 are passed through reboiler 91 prior to leaving the column 90 as the liquid hydrocarbon product stream 15. Heat is added to raise the temperature of the bottom liquid passing through reboiler 90 to strip via evaporation any remaining lower boiling point lighter hydrocarbons, including ethane, while not evaporating the higher boiling point propane and heavier hydrocarbons which form product stream 15 which exits at the bottom of the fractionation column 90 at a temperature of 147° F. and a pressure of 252 psia.

The residual stream 14 from the fractionation column 90 comprises the residual gas, typically mostly methane, from the separation process and exits the upper region of column 90 at a temperature of −130° F. and 249 psia. The residual stream 14 is passed through heat exchanger 26 to cool the vapor stream 8 leaving the separator vessel 30 and thence through heat exchanger 25 to cool the pressurized feed gas stream 3 being supplied to the separator vessel 30. In the process of cooling the vapor stream 8 and the feed gas stream 3, the residual stream 14 is heated to a temperature of 100° F. at a pressure of 239 psia.

The heated residual gas stream 19 leaving the downstream heat exchanger 25 is compressed via recompressor 50 to provide a pressurized residual gas stream 20 having a pressure of 490 psia and a temperature of 231° F. The recompressor 50 serves to raise the pressure of the residual gas stream, which constitutes the process gas feed stream 1 less the recovered heavier hydrocarbon liquid product stream 15, back to the pressure level of the incoming gas feed stream 1.

In order to evaluate the propane recovery potential of the process of the present invention, a computer simulation of the cryogenic separation process was made. In this computer simulation, the thermodynamic data used was Soave-Redlich-Kwong (SRK) K-value, enthalpy and entropy data. The efficiency of each of the work-expanders 40 and 42 was assumed to be 80%, the efficiency of each of the compressors 41 and 43 was assumed to be 74%, the efficiency of the recompressor 50 was assumed to be 75%, and work-expander bearing losses were assumed to be 4% of total power. Additionally, a minimum temperature approach of 5° F. was used on all heat exchangers in calculating heat transfer performance.

Further, the fractionation column 90 used in the computer simulation had twenty theoretical stages and the power extracted from the work-expanders 40 and 42 was used to power the feed gas compressors 41 and 43 rather than to power the recompressor 50 to boost the residual gas stream to its desired outlet pressure of 490 psia. The vapor stream 5 from the separator 30 was also split between vapor stream 7 and vapor stream 8 in the computer simulation to optimize propane recovery. It has been determined that the optimal split of the vapor stream 5 from the separator 30 results when the vapor stream 7 constitutes from about 40% to about 60% of vapor stream 5. Additionally, the ethane content of the product stream 15 was controlled at 2 mol percent.

The inlet gas stream 1 used in the computer simulation had the following composition:

| | |
|---|---|
| Helium | .10 |
| Nitrogen | 1.26 |
| Carbon Dioxide | .32 |
| Methane | 90.56 |
| Ethane | 4.37 |
| Propane | 2.23 |
| Isobutane | .30 |
| Normal Butane | .57 |
| Isopentane | .12 |
| Normal Pentane | .11 |
| Hexane | .04 |
| Heptane Plus | .02 |

Figure 2:
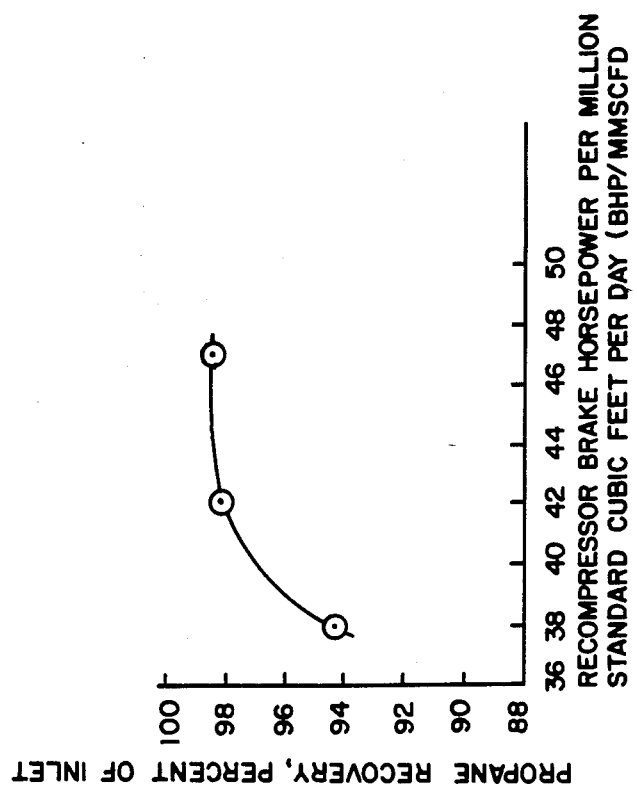
FIG. 2 is a graphical representation showing the efficiency of power recovery versus the recompressor brake horsepower expended per million standard cubic feet per day (BHP/MMSCFD) with the process of the present invention.

The performance predictions generated by such computer simulation are presented in FIG. 2 as a curve of propane recovery efficiency, expressed as a percent of propane in the feed gas stream 1, versus recompressor brake horsepower per million standard cubic feet per day (BHP/MMSCFD). The recompressor brake horsepower expended per million standard cubic feet gas flow per day is measure of the power required to return the pressure of the residual gas stream 20 to the pressure of the inlet gas stream 1. As such, a plot of the propane recovery efficiency versus recompressor brake horsepower provides a measure of the economic efficiency and potential of the process. As seen in FIG. 2, the process of the present invention results in superior propane recovery efficiencies of at least 98% from recompressor power expenditures of as little as 42 brake horsepower per million standard cubic feet per day. The propane recovery for the conditions described hereinbefore with reference to the process of the present invention illustrated in FIG. 1 is 98.4% of the propane content of the inlet gas stream 1.

As illustrated in the drawing, the pressurized feed gas stream 3 is cooled prior to admittance to the separator 30 by passing in heat exchange relationship with the residual stream 14 from the fractionation column 90. This cooling is necessary in carrying out the process of the present invention in order to cause a partial condensation of the heavier hydrocarbons in the feed gas. In the event that the feed gas is particularly rich in propane and heavier hydrocarbons, it may be desirable to use supplemental refrigeration in addition to cooling via the residual gas stream 14 in order to optimally lower the temperature of the pressurized feed gas stream 3. This could be accomplished by splitting the pressurized feed gas stream 3 into two portions, one which is cooled via heat exchange with the residual gas stream 14 and one which is cooled via supplemental refrigeration.

The process of the present invention can also be modified to recover a portion of the ethane in the feed gas by modifying the operating conditions of reboiler 91 such that the bottom liquid passing through reboiler 91 is heated to a temperature less than the boiling point of ethane at the existing liquid pressure. In this manner, the more volatile lighter hydrocarbons such as methane would be stripped from the liquid in reboiler 91 by evaporation to yield a product stream rich in propane and heavier hydrocarbons and also containing a portion of the ethane in feed gas.

It will be recognized by those skilled in the art that in the practice of the present invention, the particular pressure and temperature of the feed streams to the separators 30 and 31, as well as other pressures and temperatures at various points in the process, will depend on the conditions and nature of the gas being processed and the desired recovery of liquid hydrocarbons from the feed stream. Accordingly, it is to be understood that the exact pressures and temperatures recited in the description of the present invention hereinbefore provided are illustrative of a best mode presently contemplated in carrying out the process of the present invention, but not limiting the process of the present invention as recited in the appended claims. Therefore, it is intended that the present invention covers those modifications thereof apparent to those skilled in the art which fall within the spirit and scope of the invention as herein claimed.

I claim:

1. A process for cryogenically separating a mixed hydrocarbon feed gas via fractionation column to recover propane and heavier hydrocarbon from lighter hydrocarbon residuals including methane and ethane, comprising:
   a. compressing the feed gas to raise the pressure of the feed gas;
   b. cooling the pressurized feed gas to a temperature of about 25° F. to partially condense the feed gas thereby forming a condensate liquid from the feed gas and a vapor portion of the feed gas;
   c. separating the feed gas condensate liquid from the vapor portion of the feed gas and passing the feed gas condensate liquid to a lower region of the fractionation column;
   d. splitting the vapor portion of the separated feed gas into a first vapor substream and a second vapor substream said first vapor substream comprising from about 40% to about 60% of the total vapor portion of the separated feed gas;
   e. expanding said first vapor substream in a first work expansion means to a lower pressure and a lower temperature so as to partially condense said first vapor substream and supplying the expanded partially condensed first vapor substream to the fractionation column at a mid-point region thereof;
   f. further cooling said second vapor substream to a lower temperature so as to partially condense said second vapor substream thereby forming a condensate liquid from the second vapor substream and a vapor portion of the second vapor substream;
   g. separating the second vapor substream condensate liquid from the vapor portion of the second vapor substream and passing the condensate liquid into the fractionation column at a region above the mid-point region at which the expanded first vapor substream is passed into the fractionation column;
   h. expanding the vapor portion of said second vapor substream in a second work expansion means to a lower pressure and a lower temperature and supplying the expanded vapor portion of said second vapor substream into the fractionation column at an upper region thereof above the region at which the second vapor substream condensate liquid is passed into the fractionation column; and
   i. heating the hydrocarbon liquid collecting in the lower region of the fractionation column sufficiently to evaporate a substantial portion of lighter hydrocarbons contained therein to produce a product hydrocarbon liquid comprising propane and heavier hydrocarbons and having an ethane content not greater than about 2 mol percent.

2. A process as recited in claim 1 wherein the overhead lighter hydrocarbon residual stream from the fractionation column is passed in heat exchange relationship with the second vapor substream to cool the second vapor substream and in heat exchange relationship with the pressurized feed gas stream to cool the pressurized feed gas stream and is thence recompressed to raise the pressure of the residual stream to approximately the pressure of the feed gas stream prior to compresssion in step (a).

3. A process as recited in claim 1 wherein the first and second work expansion means each drive a compressor for compressing the feed gas to raise the pressure of the feed gas.

* * * * *